United States Patent [19]

Hirota et al.

[11] Patent Number: 4,902,705

[45] Date of Patent: Feb. 20, 1990

[54] IMIDAZOLE DERIVATIVES, AN ANTIBACTERIAL AND ANTIFUNGAL AGENT COMPRISING SAID DERIVATIVES, AND A PROCESS FOR THE PRODUCTION OF SAID IMIDAZOLE DERIVATIVES

[75] Inventors: Yohjiro Hirota, Tokyo; Hisao Sugiura; Nobuyuki Kuroda, both of Yamaguchi; Takuo Wada; Kazukuki Tsujimoto, both of Kanagawa, all of Japan

[73] Assignees: UBE Industries, Ltd.; Hokko Chemical Industry Co., Ltd., both of Japan

[21] Appl. No.: 90,684

[22] PCT Filed: Dec. 12, 1985

[86] PCT No.: PCT/JP85/00683

§ 371 Date: Jul. 21, 1987

§ 102(e) Date: Jul. 21, 1987

[87] PCT Pub. No.: WO87/03591

PCT Pub. Date: Jun. 18, 1987

[51] Int. Cl.$^4$ ............... G07D 405/12; A01N 43/50
[52] U.S. Cl. ........................... 514/397; 548/336
[58] Field of Search ................... 548/336; 514/397

[56] References Cited

U.S. PATENT DOCUMENTS 4,500,536  2/1985  Yoshida et al. ............ 548/336

FOREIGN PATENT DOCUMENTS 109568  6/1985  Japan ................ 548/336

Primary Examiner—Mary C. Lee
Assistant Examiner—Z. Northington-Davis
Attorney, Agent, or Firm—Larson and Taylor

[57] ABSTRACT

Imidazole derivatives which were provided as the new compound according to this invention and are represented by the formula:

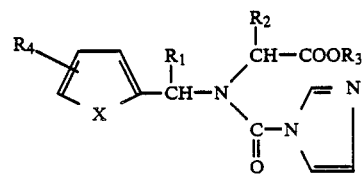

wherein $R_1$ denotes a hydrogen atom or a lower alkyl group, $R_2$ denotes a lower alkyl group, $R_3$ denotes an alkenyl group, a cycloalkyl group, an alkoxyalkyl group or a higher alkyl group, $R_4$ denotes a hydrogen atom or a lower alkyl group, and X denotes an oxygen atom or a sulfur atom, exhibit excellent antibacterial and antifungal activities against various kinds of microorganisms pathogenic to plants. The new imidazole derivatives according to this invention are useful especially as an agent for disinfecting the seeds.

8 Claims, No Drawings

IMIDAZOLE DERIVATIVES, AN ANTIBACTERIAL AND ANTIFUNGAL AGENT COMPRISING SAID DERIVATIVES, AND A PROCESS FOR THE PRODUCTION OF SAID IMIDAZOLE DERIVATIVES

TECHNICAL FIELD

This invention relates to new imidazole derivatives showing the antibacterial and antigungal activities against such microorganisms pathogenic to plants. This invention also relates to an antibacterial and antigungal agent of the agricultural and horticultural utilities, comprising said new imidazole derivative as the active ingredient.

Further, this invention relates to a process for the production of the new imidazole derivatives which show the antibacterial and antifungal activities against such microorganisms pathogenic to plants.

BACKGROUND ART

Various imidazole derivatives have already been known. Japanese patent application first publication (KOKAI) No. 150590/83 discloses N,N'-substituted azolecarboxamide derivatives represented by the formula:

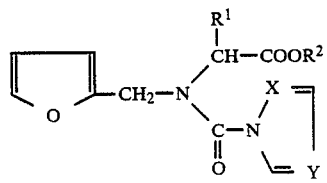

wherein $R^1$ denotes a hydrogen atom, methyl group or ethyl group, $R^2$ denotes a lower alkyl group, X and Y each denote a carbon atom or a nitrogen atom, provided that when X is a nitrogen atom, Y is a nitrogen atom or a carbon atom, and when X is a carbon atom, Y is a nitrogen atom, as the imidazole compounds having the antibacterial and antigungal activities against such microorganisms pathogenic to plants.

With these known imidazole derivatives as disclosed in said Japanese patent application first publication (KOKAI) No. 150590/83, they can be expected to show their effects of controlling the plant diseases such as cucumber powdery mildew, cucumber scab and the like, when they are applied to the infested plants as a solution containing a high concentration of said imidazole derivatives in the range of 250 to 500 ppm. as a solution containing a lower concentration of said imidazole derivatives in the range of 100 to 10 ppm. to the infested plants, they can hardly exhibit their effects of controlling the plant diseases.

Further, these known imidazole derivatives have substantially no effect for disinfecting the seeds, so that they cannot be utilized as the agent for disinfecting the seeds for the purpose of controlling "bakanae" disease and brown spot of rice plants.

An object of this invention is to provide new imidazole derivatives which can be used as a substitute for the known imidazole derivatives, and which are applicable as more useful antibacterial and antigungal agent of agricultural and horticultural utilities and, particularly also as the agent for disinfecting the seeds to control "Bakanae? disease and brown spot of rice plants. Another objects of this invention is to provide an antibacterial and antifungal agents of agricultural and horticultural utilities, comprising said new imidazole derivatives as the active ingredient. Further object of this invention is to provide a process for the production of said imidazole derivatives.

We, the present inventors, have synthetized a lot of new imidazole derivatives which are similar to the known imidazole derivatives mentioned above, in respect of their basic chemical structure but which are bearing such substituent(s) different from the substituent(s) on said known imidazole derivatives. We have extensively studied these new compounds for their biological activities. As a result, we have found that new imidazole derivatives represented by the general formula (I)

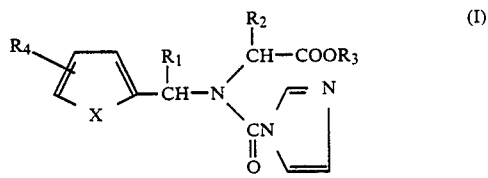

wherein $R_1$ denotes a hydrogen atom or a lower alkyl group, $R_2$ denotes a lower alkyl group, $R_3$ denotes an alkenyl group, a cycloalkyl group, an alkoxy alkyl group or a higher alkyl group, $R_4$ denotes a hydrogen atom or a lower alkyl group, and X denotes an oxygen atom or a sulfur atom, have excellent antibacterial and antifungal activities and that these compounds are more excellent and effective as the antibacterial and antifungal agent of the agricultural and horticultural utilities.

DISCLOSURE OF THE INVENTION

According to the first aspect of this invention, there is provided an imidazole derivative represented by the general formula (I)

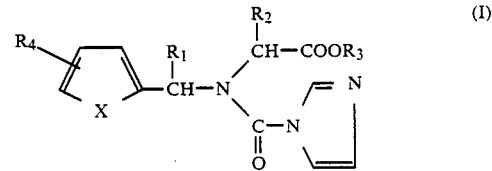

wherein $R_1$ denotes a hydrogen atom or a lower alkyl group, $R_2$ denotes a lower alkyl group, $R_3$ denotes an alkenyl group, a cycloalkyl group, an alkoxyalkyl group or a higher alkyl group, $R_4$ denotes a hydrogen atom or a lower alkyl group, and X denotes an oxygen atom or a sulfur atom.

For the compound of the formula (I) above where $R_1$, $R_2$ and $R_4$ each denote a lower alkyl group, the lower alkyl group may be a lower alkyl group containing 1 to 6 carbon atoms, such as methyl group, ethyl group, propyl group, isopropyl group, butyl group, isobutyl group, secondary butyl group, tertiary butyl group, pentyl group, hexyl group, isohexyl group and the like. When $R_3$ is a lower alkenyl group, this lower alkenyl group may be an alkenyl group containing 2 to 10 carbon atoms, such as vinyl group, allyl group, 1-propenyl group, 2-methyl-2-propenyl group, 1-methyl-2-propenyl group, 2-butenyl group, 3-butenyl group, 2-pentenyl group, 2,4-hexadienyl group, hexenyl group and the like. The cycloalkyl group for $R_3$ may be a cycloalkyl group containing 3 to 6 carbon atoms, and it may preferably be a cyclopentyl group or cyclohexyl group. When $R_3$ is an alkoxyalkyl group, it may be a lower alkoxy-lower alkyl group containing 2 to 6 carbon atoms. Preferred examples of the alkoxyalkyl groups for $R_3$ include methoxymethyl group, ethoxymethyl group, propoxymethyl group, methoxyethyl group, ethoxyethyl group and propoxyethyl group.

When $R_3$ denotes a higher alkyl group, it may be an alkyl group containing 10 to 20 carbon atoms. Examples of such higher alkyl group may be decyl group, undecyl group, dodecyl group, tridecyl group, tetradecyl group, pentadecyl group, heptadecyl group, octadecyl group, nonadecyl group and cicocyl group.

According to the second aspect of this invention, there is provided an antibacterial and antifungal agent of agricultural and horticultural utilities, comprising as the active ingredient an imidazole derivative represented by the formula (I)

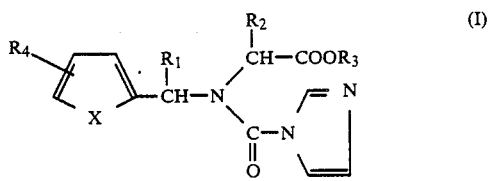

wherein $R_1$ denotes a hydrogen atom or a lower alkyl group, $R_2$ denotes aa lower a;lyl group, $R_3$ denotes an alkenyl group, a cycloalkyl group, an alkoxyalkyl group or a higher alkyl group, $R_4$ denotes a hydrogen atom or a lower alkyl group, and X denotes an oxygen atom or a sulfur group.

The compounds of the above-mentioned general formula (I) exhibit the effects for controlling the infesting microorganisms such as those of rice blast, rice brown spot, rice seath blight, tomato late blight, cucumber powdery mildew, cucumber gray mold, barley powdery mildew, kidney bean stem rot, wheat brown rust and the like when they are applied to the infected plants. Furthermore, these compounds of the formula (I) exhibit the effects for sterilizing the seeds to prevent the plant diseases such as rice "bakanae" disease and rice brown spot. Pathogenic microorganisms in the soil, such as those causing the damping-off disease of beet can also be controlled by treating the soil with the compounds of the formula (I) according to this invention. The effects of the compounds of this invention for controlling the plant diseases are not be limited to the effects of controlling the particular examples of the diseases specified above, and various diseases of rice, barley and wheat, vegetables, fruit trees and the like can effectively be controlled by applying the compounds of this invention onto the foliage of the plants, by disinfecting the seeds or by treating the soil with the compound.

The antimicrobial agent of the agricultural and horicultural utilities according to the second aspect of this invention may be formulated into various types of preparations such as dust, wettable powder, emulsifiable concentrate granules, fine granules and other conventional formulation forms. In preparing these formulation in the different forms, the carrier to be used may be any of the liquid or solid carriers and not be limited to specific ones. For example, solid carriers may be various grades of clays, kaoline, clay, diatomaceous earth, talc, silica and the like. Liquid carriers may be a liquid which can be a solvent for dissolving the imidazole derivative compounds of the formula (I), or a liquid which itself cannot be a solvent for dissolution of said imidazole compounds but can disperse or dissolve therein said imidazole compounds with aid of an adjuvant. For example, benzene, xylene, toluene, kerosin, alcohols, ketones, dimethylsulfoxide, dimethylformamide and the like are available for this purpose. Appropriate surface-active agents and other adjuvants such as spreading agent and sticking agent may be mixed with said organic liquids so that the mixture may be formulated into aqueous solutions or emulsions. The antimicrobial composition containing the imidazole compound of the general formula (I) may further contain other additives such as other antimicrobial agents, insecticides, herbicides and plant-growth-regulating agents for the reduction of labor power and for ensuring the controlling effects of the imidazole compounds.

According to the third aspect of this invention, there is provided a process for the production of an imidazole derivative represented by the formula (I):

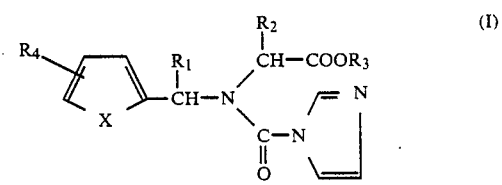

wherein $R_1$ is a hydrogen atom or a lower alkyl group, $R_2$ is a lower alkyl group, $R_3$ is an alkenyl group, a cycloalkyl group, an alkoxyalkyl group or a higher alkyl group, $R_4$ is a hydrogen atom or a lower alkyl group, and X is an oxygen atom or a sulfur atom, which comprises reacting a carbamoyl chloride compound of the formula (II):

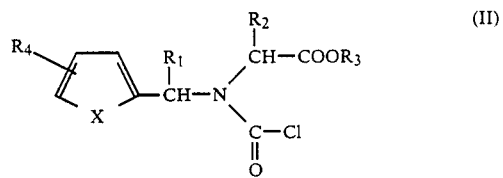

wherein $R_1$, $R_2$, $R_3$, $R_4$ and X are as defined above, with imidazole of the formula (III):

in an organic solvent which is unreactive in the reaction involved.

In the process according to the third aspect of this invention, the reaction of the carbamoyl chloride compound of the formula (II) with imidazole of the formula (III) may preferably be conducted in the presence of a base such as carbonate, a hydrogen carbonate or a hydroxide of an alkali metal, or a trialkylamine and pyridine.

Preferred examples of such bases include basic compounds such as potassium carbonate, sodium hydrogen carbonate, sodium hydroxide, triethylamine and pyridine. Examples of the organic solvent to be used as the reaction medium may be an unreactive solvent such as acetone, methylethylketone, acetonitrile, dimethyl-formamide, dimethylsulfoxide or dioxane. The amount of imidazole used for this reaction may preferably be in a range of 1.0 to 5.0 mol. per 1 mol. of the carbamoyl chloride compound of the general formula (II), and the base may preferably be used in an amount of 0.5 to 5.0 mol. per 1 mol. of the carbamoyl chloride compound of the general formula (II). This reaction is performed at a temperature of 20° to 150° C. preferably of 50° to 120° C.

The starting carbamoyl chloride compound of the general formula (II) above may easily be synthetized by reacting a secondary amine represented by the formula (IV):

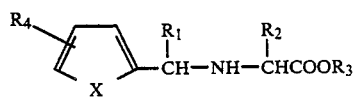

wherein $R_1$, $R_2$, $R_3$, $R_4$ and X are as defined above, with phosgene ($COCl_2$) or with trichloromethyl chloroformate of the formula (V):

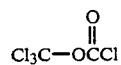

in an organic solvent which is unreactive in the reaction. The reaction for this synthesis is depicted by the following reaction equation (1) or (2);

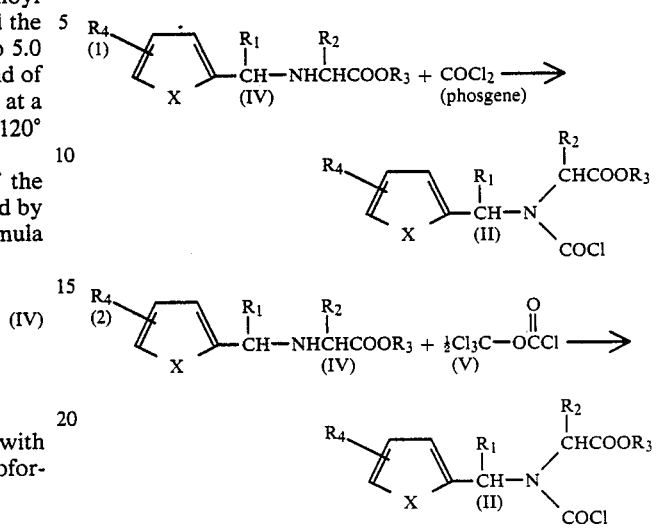

BEST MODE OF WORKING THE INVENTION

Representative examples of the imidazole derivative compounds of the general formula (I) according to the first aspect of this invention are listed in Table 1 below:

TABLE 1

| Compound No. | X | $R_1$ | $R_2$ | $R_3$ | Physical data (Refractive index or Melting point) |
|---|---|---|---|---|---|
| 1 | furan | H | $-C_2H_5$ | $\begin{array}{c}C_2H_5\\ \mid\\ -CHCH=CH_2\end{array}$ | $n_D^{16}$ 1.5193 |
| 2 | " | " | " | $-CH_2CH_2OC_2H_5$ | $n_D^{22}$ 1.5062 |
| 3 | " | " | $-C_3H_7-n$ | $-(CH_2)_3CH=CH_2$ | $n_D^{21}$ 1.5112 |
| 4 | " | " | " | $\begin{array}{c}CH_3\\ \mid\\ -CHCH=CH_2\end{array}$ | $n_D^{21}$ 1.5157 |
| 5 | " | " | $-C_2H_5$ | $-(CH_2)_2CH=CH_2$ | $n_D^{20}$ 1.5180 |
| 6 | " | " | $-C_3H_7-n$ | " | $n_D^{20}$ 1.5018 |
| 7 | " | " | $-C_2H_5$ | $-(CH_2)_3CH=CH_2$ | $n_D^{20}$ 1.5163 |
| 8 | " | " | " | $\begin{array}{c}CH_3\\ \mid\\ -CHCH=CH_2\end{array}$ | $n_D^{17}$ 1.5198 |
| 9 | " | " | " | $-C_{12}H_{25}-n$ | $n_D^{28}$ 1.4959 |
| 10 | " | " | " | $-C_{14}H_{29}-n$ | $n_D^{15}$ 1.4942 |
| 11 | furan | H | $-CH_3$ | $-CH_2CH=CH_2$ | $n_D^{23}$ 1.5242 |
| 12 | " | " | $-C_3H_7-i$ | " | $n_D^{23}$ 1.5149 |

TABLE 1-continued

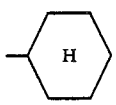
(I)

| Compound No. | R4 / X | R1 | R2 | R3 | Physical data (Refractive index or Melting point) |
|---|---|---|---|---|---|
| 13 | " | " | —C₃H₇—n | —CH₂—CH=CHCH₃ | $n_D^{21}$ 1.5174 |
| 14 | " | " | —C₂H₅ | " | $n_D^{19}$ 1.5217 |
| 15 | " | " | —C₄H₉—n | —CH₂CH=CH₂ | $n_D^{27}$ 1.5123 |
| 16 | " | " | —C₃H₇—n |  | $n_D^{26}$ 1.5147 |
| 17 | " | " | —C₃H₇—n | —CH₂CH=CH₂ | $n_D^{19}$ 1.5191 |
| 18 | " | " | —C₂H₅ | 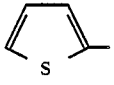 | $n_D^{20}$ 1.5187 |
| 19 | " | " | —C₂H₅ | —CH₂CH=CH₂ | m.p. 69–71° C. |
| 20 | 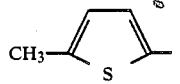 | " | —C₃H₇—n | —(CH₂)₂CH=CH₂ | $n_D^{21}$ 1.5423 |
| 21 | 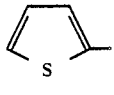 | " | —C₂H₅ | —CH₂CH=CH₂ | $n_D^{23}$ 1.5436 |
| 22 | 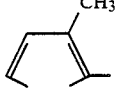 | " | —C₂H₅ | —C₁₄H₂₉—n | $n_D^{15}$ 1.5100 |
| 23 | " | —CH₃ | " | —CH₂CH=CH₂ | $n_D^{23}$ 1.5444 |
| 24 | " | H | —C₃H₇—n | —(CH₂)₃CH=CH₂ | $n_D^{21}$ 1.5353 |
| 25 | 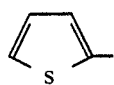 | H | —C₂H₅ | —CH₂CH=CH₂ | $n_D^{20}$ 1.5454 |
| 26 | 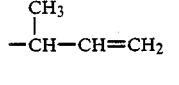 | " | —C₃H₇—n | —CH(CH₃)—CH=CH₂ | $n_D^{21}$ 1.5420 |
| 27 | " | " | —C₂H₅ | —(CH₂)₂CH=CH₂ | $n_D^{20}$ 1.5429 |
| 28 | " | " | " | —CH₂CH=CH—CH₃ | $n_D^{21}$ 1.5401 |
| 29 | " | " | " | —(CH₂)₃CH=CH₂ | $n_D^{17}$ 1.5397 |
| 30 | " | " | " | —CH(CH₃)—CH=CH₂ | $n_D^{21}$ 1.5474 |
| 31 | " | " | —C₃H₇—n | —CH₂CH=CHCH₃ | $n_D^{21}$ 1.5420 |
| 32 | " | " | —C₂H₅ | —C₁₂H₂₅—n | $n_D^{28}$ 1.5106 |
| 33 | " | " | —CH₃ | —CH₂CH=CH₂ | $n_D^{20}$ 1.5482 |
| 34 | " | " | —C₃H₇—n | 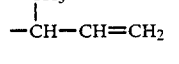 | $n_D^{23}$ 1.5358 |

TABLE 1-continued $$\underset{R_4}{\overset{}{\bigotimes}}_X\overset{R_1}{\underset{CH-N}{\mid}}\overset{\overset{R_2}{\mid}}{\underset{C-N}{\overset{CH-COOR_3}{\mid}}}\overset{}{\underset{\parallel}{\overset{}{\bigotimes}}}$$ (I)

| Compound No. | $\underset{R_4}{\overset{}{\bigotimes}}_X$ | X | $R_1$ | $R_2$ | $R_3$ | Physical data (Refractive index or Melting point) |
|---|---|---|---|---|---|---|
| 35 | | " | " | $-C_3H_7-n$ | $-CH_2CH=CH_2$ | $n_D^{27}$ 1.5252 |
| 36 | | " | " | $-C_2H_5$ | cyclopentyl-H | $n_D^{24}$ 1.5399 |
| 37 | | " | " | " | $-CH_2CH=CH_2$ | $n_D^{21}$ 1.5476 |

The Compound Number shown in Table 1 above is referred to in the Examples given hereinafter.

The process for the production of the compounds of the formula (I) according to this invention is now illustrated with reference to the Examples below.

EXAMPLE 1

Preparation of N-1-(1-cyclohexyloxycarbonylbutyl)-N-(1-imidazolylcarbonyl)-furfurylamine (Compound No. 16)

N-1-(1-cyclohexyloxycarbonylbutyl)-N-furfurylcarbamoyl chloride (4 g, 0.012 mol.) was dissolved in dimethylsulfoxide (50 ml), to which were added imidazole (2.5 g, 0.037 mol) and triethylamine (1.5 g, 0.015 mol). The mixture obtained was stirred for 30 minutes at 100° C. under heating. After completion of the reaction, the reaction mixture was admixed with water and extracted with toluene. The organic solvent layer separated was concentrated and purified by column-chromatography to afford the titled compound as a yellowish orange colored liquid (2.8 g).

EXAMPLE 2

Preparation of N-1-(1-allyloxycarbonylpropyl)-N-(1-imidazolylcarbonyl)-furfurylamine (Compound No. 19)

N-1-(1-allyloxycarbonylpropyl-N-furfuryl-carbamoyl chloride (10 g, 0.033 mol) was dissolved in N,N-dimethylformamide (100 ml), to which were added imidazole (10 g, 0.15 mol) and potassium carbonate (5g, 0.036 mol). The mixture was stirred for 1 hour at 70° C. under heating. After completion of the reaction, the reaction mixture was admixed with water and extracted with toluene. The organic solvent layer separated was concentrated and the resultant residue was recrystallized from a solvent mixture of toluene-n-hexane to afford the titled compound as colorless crystals (9.2 g).

EXAMPLE 3

Preparation of N-1-(1-allyloxycarbonylbutyl)-N-(1-imidazolylcarbonyl)-2-thienylmethylamine (Compound No. 35)

N-1-(1-allyloxycarbonylbutyl)-N-2-thienylmethyl-carbamoyl- chloride (3.2 g, 0.010 mol) was dissolved in acetonitrile (50 ml), to which were added imidazole (0.9 g, 0.013 mol) and pyridine (3.5 g, 0.044 mol). The mixture was heated for 2 hours at 80° C. After completion of the reaction, the reaction mixture was processed in a same manner as in the Example 1, to obtain the titled compound as a yellowish orange colored liquid (1.5 g).

Some Examples are now given below to illustrate the uses of the imidazole compounds of the general formula (I) as the antibacterial, antifungal agent of the agricultural and horticultural utilities.

EXAMPLE-4 (DUST)

2 Parts of Compound No. 17 identified hereinbefore and 98 parts of clay were mixed and milled uniformly to yield a dust preparation containing 2% of the active ingredient.

EXAMPLE 5 (WETTABLE POWDER)

30 Parts of Compound No. 11 identified hereinbefore, 3 parts of calcium alkylbenzenesulfonates, 5 parts of polyoxyethylenenonylphenylether and 62 parts of China clay were mixed and milled uniformly to obtain a finely divided, homogeneous wettable powder containing 30% of the active ingredient. For practical use, the wettable powder thus prepared may be diluted with water to a volume of 600 to 1000 folds larger than the original volume, for being sprayed onto the plants.

EXAMPLE 6 (EMULSION)

30 Parts of Compound No. 15 identified hereinbefore, 40 parts of methylethylketone and 30 parts of polyoxyethylenenonylphenylether were mixed to give a solution, so that an emulsifiable concentrate containing 30% of the active ingredient was obtained. When used as the antimicrobial agent, the emulsifiable concentrate thus prepared may be diluted with water to a volume of 600 to 1000 folds larger than the original volume, for being sprayed onto the plants.

EXAMPLE 7 (GRANULES)

A mixture of 5 parts of Compound No. 5 listed hereinbefore, 1.5 parts of lauryl sulfate, 1.5 parts of calcium ligninesulfonate, 25 parts of bentonite and 67 parts of white clay was further admixed with 15 parts of water. The resultant mixture was kneaded in a kneader. The mixture was then granulated and dried in a fluidizing, drying apparatus to obtain granules containing 5% of the active ingredient.

The following Test Examples illustrate the controlling effects of the imidazole derivative compounds of the formula (I) when applied as the antimicrobial agent of the agricultural and horticultural utilities. In the comparative tests of the following Test Examples, there were used as the Comparative compound some compounds which are disclosed in the Japanese patent application first publication (KOKAI) No. 150590/83 and which have respectively the following chemical formulas:

Comparative Compound No. 1

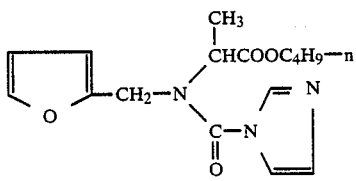

Comparative Compound No. 2

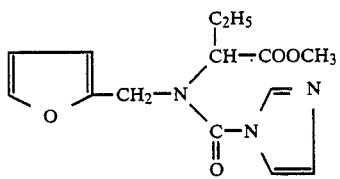

Comparative Compound No. 3

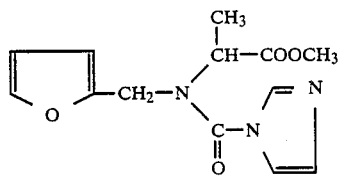

TEST EXAMPLE 1

Tests For Controlling Rice Blast

Seedlings of paddy rice plant (variety: Asahi) as grown to the third leaf stage, which had been cultured in non-irrigated soil in unglazed pots (9 cm in diameter) in a green house, were sprayed with test solutions. Each of these test solutions had been prepared by diluting with water to the predetermined concentration of the active ingredient such a wettable powder which was formulated according to the Example 5 and which contained a test compound indicated in Table 2 as the active ingredient. One day after the spraying of the test solution, a suspension of spores of the pathogenic microorganism of rice blast (*Pyricularia oryzae*) was sprayed over the paddy rice seadlings for inoculation. After the inoculation, the seedlings in the pots were placed and maintained overnight under the conditions of a humid chamber (where a humidity of 95 to 100% and a temperature of 24° to 25° C. prevailed). Five days after the inoculation, the number of the lesions per leaf on the third leaf of the rice plant was counted, and the rate (%) of the controlling effects of the tested compound was evaluated according to the following equation. Degree of phytotoxicity to the rice plant was estimated according to the following index. The test results are shown in Table 2.

Rate (%) of the controlling effects =

$$\left(1 - \frac{\text{Number of the lesions in the treated plot}}{\text{Number of the lesions in the untreated plot}}\right) \times 100$$

Index for phytotoxicity:
5: Very severe
4: Severe
3: Moderate
2: Slight
1: Negligible
0: None

TABLE 2

| Test compound No. | Concentration of active ingredient in the sprayed solution (ppm) | Rate of controlling effect (%) | Degree of phytotoxicity |
|---|---|---|---|
| 12 | 200 | 90 | 0 |
| 13 | 200 | 100 | 0 |
| 14 | 200 | 100 | 0 |
| 25 | 200 | 100 | 0 |
| Comparative tests | | | |
| Comparative compound No. 1 | 200 | 0 | 0 |
| Comparative compound No. 2 | 200 | 50 | 0 |
| Comparative compound No. 4 (IBP) | 480 | 72 | 0 |
| Untreated | — | 0 (25) | — |

Note 1: The Comparative compound No. 4 (IBP) is a commercially available fungicidal agent containing S—benzyl O,O—diisopropyl phosphorothioate.
Note 2: The figure given in the parenthesis shows an averaged number of the lesions per leaf in the untreated plot.

TEST EXAMPLE 2

Tests For Controlling Rice Brown Spot

Seadlings of paddy rice plant (variety: Asahi) as grown to the fourth true leaf stage, which had been cultured in the non-irrigated soil in unglazed pots (9 cm in diameter) in a green house, were sprayed with the test solutions which had been diluted with water to a predetermined concentration of the active ingredient. One day after the spraying, a suspension of conidiospores of the pathogenic microorganisms of rice brown spot (*Cochliobolus miyabeanus*) was sprayed over the seedlings for inoculation. Five days after the inoculation, the number of the lesions per leaf on the fourth true leaf of the rice plant was counted, and the rate (%) of the controlling effects of the tested compound was evaluated according to the following equation. Degree of phytotoxicity to the rice plant was estimated in the same manner as the Example 1. The test results are shown in Table 3 below.

Rate (%) of the controlling effects =

$$\left(1 - \frac{\text{Number of the lesions in the treated plot}}{\text{Number of the lesions in the untreated plot}}\right) \times 100$$

TABLE 3

| Test Compound No. | Concentration of active ingredient in the sprayed solution (ppm) | Rate of controlling effects (%) | Degree of phytotoxicity |
| --- | --- | --- | --- |
| 1 | 200 | 100 | 0 |
| 2 | 200 | 100 | 0 |
| 3 | 200 | 100 | 0 |
| 5 | 200 | 100 | 0 |
| 8 | 200 | 100 | 0 |
| 11 | 200 | 100 | 0 |
| 12 | 200 | 100 | 0 |
| 13 | 200 | 100 | 0 |
| 14 | 200 | 100 | 0 |
| 15 | 200 | 100 | 0 |
| 16 | 200 | 95 | 0 |
| 17 | 200 | 97 | 0 |
| 18 | 200 | 100 | 0 |
| 19 | 200 | 98 | 0 |
| 20 | 200 | 98 | 0 |
| 21 | 200 | 100 | 0 |
| 23 | 200 | 100 | 0 |
| 24 | 200 | 100 | 0 |
| 25 | 200 | 100 | 0 |
| 26 | 200 | 80 | 0 |
| 27 | 200 | 100 | 0 |
| 28 | 200 | 100 | 0 |
| 29 | 200 | 95 | 0 |
| 30 | 200 | 100 | 0 |
| 31 | 200 | 100 | 0 |
| 33 | 200 | 100 | 0 |
| 35 | 200 | 100 | 0 |
| 36 | 200 | 100 | 0 |
| 37 | 200 | 100 | 0 |
| Comparative tests | | | |
| Comparative compound No. 1 | 200 | 0 | 0 |
| Comparative compound No. 2 | 200 | 0 | 0 |
| Comparative compound No. 5 (Iprodione) | 200 | 98 | 0 |
| Untreated | — | 0 (53) | — |

Note 1: The Comparative compound No. 5 (Iprodione) is a commercially available fungicidal agent containing 3-(3,5-dichlorophenyl)-N—isopropyl-2,4-dioxoimidazolidine-1-carboxamide.
Note 2: The figure given in the parenthesis shows an averaged number of the lesions per leaf in the untreated plot.

TEST EXAMPLE 3

Tests For Controlling Barley Powdery Mildow

Seedlings of barley (variety: Azuma Golden) as grown to the first leaf stage, which had been cultured in the soil in unglazed pots (9 cm in diameter) in a green house, were sprayed with test solutions at a rate of 10 ml per 2 pots. Each of the test solutions sprayed had been prepared by diluting the wettable powder as prepared according to the Example 5, with water to the predetermined concentration of the active ingredient. The next day after the treatment, the inoculation was made by lightly scattering the spores of barley powdery mildew (*Erysiphe graminis Sp. hordei*) which had previously been developed on the leaves of barley, onto the treated leaves of barley plants. Seven days after the inoculation, the number of the fungal colonies of barley powdery mildew per leaf was assessed, and the rate (%) of the controlling effects of the tested compound was evaluated according to the following equation.

Degree of phytotoxicity to barley was estimated according to the index similar to the Test Example 1.

Rate (%) of the controlling effects =

$$\left(1 - \frac{\text{Number of the colonies per leaf in the treated plot}}{\text{Number of the colonies per leaf in the untreated plot}}\right) \times 100$$

The results are shown in Table 4 below.

TABLE 4

| Test Compound No. | Concentration of active ingredient in the sprayed solution (ppm) | Rate of controlling effect (%) | Degree of phytotoxicity |
| --- | --- | --- | --- |
| 1 | 100 | 100 | 0 |
| 2 | 100 | 100 | 0 |
| 3 | 100 | 100 | 0 |
| 4 | 100 | 100 | 0 |
| 5 | 100 | 100 | 0 |
| 6 | 100 | 100 | 0 |
| 7 | 100 | 98 | 0 |
| 9 | 100 | 95 | 0 |
| 10 | 100 | 100 | 0 |
| 11 | 100 | 100 | 0 |
| 12 | 100 | 100 | 0 |
| 13 | 100 | 100 | 0 |
| 14 | 100 | 97 | 0 |
| 15 | 100 | 100 | 0 |
| 16 | 100 | 97 | 0 |
| 18 | 100 | 95 | 0 |
| 20 | 100 | 100 | 0 |
| 21 | 100 | 100 | 0 |
| 22 | 100 | 100 | 0 |
| 23 | 100 | 100 | 0 |
| 24 | 100 | 100 | 0 |
| 25 | 100 | 100 | 0 |
| 26 | 100 | 100 | 0 |
| 27 | 100 | 100 | 0 |
| 28 | 100 | 96 | 0 |
| 29 | 100 | 100 | 0 |
| 30 | 100 | 100 | 0 |
| 31 | 100 | 100 | 0 |
| 32 | 100 | 100 | 0 |
| 33 | 100 | 98 | 0 |
| 34 | 100 | 99 | 0 |
| 35 | 100 | 93 | 0 |
| 37 | 100 | 96 | 0 |
| Comparative tests | | | |
| Comparative compound No. 1 | 100 | 0 | 0 |
| Comparative compound No. 3 | 100 | 0 | 0 |
| Comparative compound No. 6 (Quinomethionate) | 100 | 85 | 0 |
| Untreated | — | 0 (100) | — |

Note 1: The Comparative compound No. 6 (Quinomethionate) is commercially available fungicidal agent containing S,S—6-methylquinoxaline-2,3-diyl.
Note 2: The figure given in the parenthesis shows an average number of the fungal colonies per leaf in the untreated plot.

TEST EXAMPLE 4

Tests For Controlling Rice Sheath Blight

Seedlings of rice plant as grown to the sixth leaf stage, which had been cultured in the soil in unglazed pots (9 cm in diameter), were sprayed with the test solutions at a rate of 40 ml per 3 pots. Each of the test solutions contained the active ingredient at a predetermined concentration. The seedlings so treated were allowed to stand in a glass green house. One day after the spraying of the test solution, the inoculation was made by placing adhesively a piece of agar disc containing the mycelium which had been punched out by a cork borer of 10 mm diameter from the edge of mycerial colony of rice sheath blight (*Rhizoctonia* solani) as cultured or potate sucrose agar medium for 48 hours at 27° C., on the bottom of the leaf sheath of the rice plant. The rice plants so treated were then kept in a humid chamber overnight. Development of the disease was estimated 6 days after the inoculation, by measuring the length of the lesion of the rice sheath blight about each stem of the rice plant, and the rate (%) of the controlling effects of the tested compound was evaluated by comparing the length of the lesion in the treated plot with that in the untreated plot. Degree of phytotoxicity was estimated in the same manner as in the Test Example 1.

Rate (%) of the controlling effects =

$$\left(1 - \frac{\text{length of the lesion in the treated plot}}{\text{length of the lesion in the untreated plot}}\right) \times 100$$

The test results are shown in Table 5.

TABLE 5

| Test compound No. | Concentration of active ingredient in the sprayed solution (ppm) | Rate of controlling effect (%) | Degree of phytotoxicity |
|---|---|---|---|
| 12 | 200 | 100 | 0 |
| 13 | 200 | 95 | 0 |
| Comparative tests | | | |
| Comparative compound No. 1 | 200 | 0 | 0 |
| Comparative compound No. 7 (Validamycin A) | 30 | 88 | 0 |
| Untreated | — | 0 (17) | — |

Note 1: The figure given in the parenthesis shows the length (cm) of the lesion in the untreated plot.

TEST EXAMPLE 5

Tests For Controlling Cucumber Gray Mold

Cucumber plants (Variety; Sagami Hanjiro) as grown to the first true leaf stage, which had been cultured in the soil in unglazed pots (9 cm in diameter) in a green house, were sprayed with the test solutions containing the test compounds as the active ingredient, at a rate of 10 ml per pot. Each of the test solutions was containing the active ingredient at a predetermined concentration and had been prepared by diluting with water a wettable powder which was formulated according to the Example 5 and containing as the active ingredient the test compound indicated in Table 6 below. One day after the spraying of the test solution, inoculation of the pathogenic fungi was performed by placing on the center of the each leaflet of the first true leaf stage such a piece of agar disc containing the mycelium which had been prepared by punching out, with a cork borer of 5 mm diameter, from the edge of the mycerial colony of cucumber gray mold (Botorytis cinera) as incubated for 2 days at 20° C. on the potate decoction agar medium. The cucumber plants thus treated were kept in a humid chamber for 3 days at 20° C. to promote the development of the cucumber gray mold fungi. Three days after the inoculation, length of the lessions of cucumber gray mold was measured with vernier caliper, and the rate (%) of the controlling effects of the test compound was evaluated according to the equation given below. Degree of the phytotoxicity to cucumber plant was estimated according to the same index as in the Test Example 1.

Rate (%) of the controlling effects =

$$\left(1 - \frac{\text{length of lesions of cucumber gray mold in the treated plot}}{\text{length of lesions of cucumber gray mold in the untreated plot}}\right) \times 100$$

The tests were conducted in two replicates for a particular concentration of the test compound, and the averaged value of the rates of the controlling effects was calculated.

The test results are shown in Table 6.

TABLE 6

| Test compound No. | Concentration of active ingredient in the sprayed solution (ppm) | Rate of the controlling effects (%) | Degree of phytotoxicity |
|---|---|---|---|
| 5 | 200 | 98 | 0 |
| 6 | 200 | 95 | 0 |
| 11 | 200 | 100 | 0 |
| 12 | 200 | 88 | 0 |
| 15 | 200 | 100 | 0 |
| 26 | 200 | 100 | 0 |
| 27 | 200 | 99 | 0 |
| 29 | 200 | 95 | 0 |
| 31 | 200 | 96 | 0 |
| Comparative tests | | | |
| Comparative compound No. 1 | 200 | 0 | 0 |
| Comparative compound No. 3 | 200 | 0 | 0 |
| Comparative compound No. 8 (Procymidone) | 200 | 98 | 0 |
| Untreated | — | 0 (34) | — |

Note 1: The Comparative compound No. 8 (Procymidone) is a commercially available fungicidal agent containing N—(3,5-dichlorophenyl)-1.2-dimethyl-cyclopropane-1,2-dicarboximide.
Note 2: The figure given in the parenthesis shows the length (mm) of the lesions in the untreated plots.

TEST EXAMPLE 6

Tests For Disinfection Of Rice Seeds Infected With Rice Bakanae Disease

The rice seeds infected with the Bakanae disease (Fusarium moniliforme) were obtained from the rice plants (Variety: Kinki No. 33) which has been inoculated by spraying a concentrated suspension of spores of Fusarium moniliforme on the plants at the flowering season. The so infected rice seeds were employed for the tests. Disinfection of the infected rice seeds was carried out as follows; Wettable powders which were formulated according to the Example 5 and each containing the test compound were diluted with water to the predetermined concentration of the active ingredient, to prepare the test solutions. The infested rice seeds were immersed in the test solution at a ratio of the rice seeds to the test solution of 1:1 (by volume/volume) for 24 hours at 20° C. for the disinfection. After the disinfection, the rice seeds were immersed in a water bath for 3 days at 20° C. for absorption of water and then for 24 hours at 30° C. for promotion of the germination.

The fully swollen rice seeds were sowed and cultivated in a nursery box containing soil granules of a trade name "Kumiai" (as produced by Kureha Chemical Co., Ltd.) according to a standard method of nursering the seedlings in box, followed by cultivation of the rice seedlings in a glass greenhouse. 25 Days after the sowing of the seeds (at the fourth leaf stage), all the seedlings in the treated plots were pulled out from the nursery box. The assessment of the outbreak of the Bakanae disease was performed in such way that the number of the disease incidence seedlings was calculated and the percentages of the disease-incidence seedlings based on the whole seedlings was determined, whereby the rate (%) of the controlling effects of the test compound was evaluated. Degree of the phytotoxicity to rice plants was also estimated according to the same standards as that in the Test Example 1.

The tests were performed in three replicates for a particular concentration of the test compound, and the averaged value for the percentages of the disinfected seeds was calculated.

The test result are shown in Table 7 below.

Percentage of the disease-incidence seedlings =

$$\frac{\text{Number of the disease-incidence seedlings}}{\text{Number of all the seedlings under test}} \times 100$$

Percentage of the sterilized seeds =

$$\left(1 - \frac{\text{percentage of the disease-incidence seedlings in the treated plot}}{\text{percentage of the disease-incidence seedlings in the untreated plot}}\right) \times 100$$

TABLE 7

| Test compound No. | Concentration of active ingredient in the test solution (ppm) | Percentages of the disinfected seeds | Degree of phytotoxicity |
|---|---|---|---|
| 1 | 1000 | 95 | 0 |
| 2 | 1000 | 96 | 0 |
| 3 | 1000 | 100 | 0 |
| 4 | 1000 | 100 | 0 |
| 5 | 1000 | 97 | 0 |
| 6 | 1000 | 98 | 0 |
| 7 | 1000 | 100 | 0 |
| 8 | 1000 | 95 | 0 |
| 11 | 1000 | 100 | 0 |
| 13 | 1000 | 100 | 0 |
| 14 | 1000 | 100 | 0 |
| 15 | 1000 | 95 | 0 |
| 17 | 1000 | 100 | 0 |
| 18 | 1000 | 100 | 0 |
| 19 | 1000 | 100 | 0 |
| 20 | 1000 | 100 | 0 |
| 21 | 1000 | 100 | 0 |
| 24 | 1000 | 100 | 0 |
| 25 | 1000 | 96 | 0 |
| 26 | 1000 | 100 | 0 |
| 27 | 1000 | 100 | 0 |
| 28 | 1000 | 95 | 0 |
| 29 | 1000 | 97 | 0 |
| 30 | 1000 | 98 | 0 |
| 31 | 1000 | 100 | 0 |
| Comparative tests | | | |
| Comparative compound No. 2 | 1000 | 60 | 0 |
| Comparative compound No. 3 | 1000 | 0 | 0 |
| Comparative compound No. 9 (Benomyl) | 1000 | 95 | 0 |
| Untreated | — | 0 | — |

TABLE 7-continued

| Test compound No. | Concentration of active ingredient in the test solution (ppm) | Percentages of the disinfected seeds | Degree of phytotoxicity |
|---|---|---|---|
| | | (57.3) | |

Note 1: The comparative compound No. 9 (Benomyl) is a commercially available fungicidal agent containing 1-(n-butylcarbamoyl)-2-benzimidazole-carbamic acid methyl ester.
Note 2: The figure given in the parenthesis shows the percentage of the disease-incidence seedlings in the untreated plots.

TEST EXAMPLE 7

Tests For Disinfection Of Rice Seeds Infected With Rice Brown Spot.

The rice seeds as naturally infected with the pathogenic fungi of rice brown spot (*Cochliobolus miyabeanns*) were obtained from the rice plants in paddy fields where the disease of rice brown spot were frequently occurring, and these infected seeds were used for the tests. The method of disinfecting the rice seeds and the other test procedures were same as those in the Test Example 6. The assessment of the out-break of the disease was made 20 days after the sowing of the seeds. The number of the seedlings which had been infested by the rice brown spot was counted, and the percentage of the disinfected seeds was evaluated in the same manner as in the preceeding tests for the disinfection of the seeds infected with the rice bakanae disease.

Degree of the phytotoxicity to rice plants was estimated according to the same standards as in the Test Example 4.

The tests were made in three replicates for each test plot, and the averaged value of the evaluated percentages of the disinfected seeds was calculated. The test results are shown in Table 8.

TABLE 8

| Test compound No. | Concentration of active ingredient in the test solution (ppm) | Percentage of the disinfected seeds | Degree of phytotoxicity |
|---|---|---|---|
| 1 | 1000 | 100 | 0 |
| 2 | 1000 | 100 | 0 |
| 3 | 1000 | 100 | 0 |
| 4 | 1000 | 100 | 0 |
| 5 | 1000 | 100 | 0 |
| 6 | 1000 | 100 | 0 |
| 7 | 1000 | 100 | 0 |
| 8 | 1000 | 100 | 0 |
| 11 | 1000 | 87 | 0 |
| 12 | 1000 | 99 | 0 |
| 13 | 1000 | 100 | 0 |
| 14 | 1000 | 100 | 0 |
| 15 | 1000 | 97 | 0 |
| 17 | 1000 | 100 | 0 |
| 18 | 1000 | 100 | 0 |
| 19 | 1000 | 100 | 0 |
| 20 | 1000 | 100 | 0 |
| 21 | 1000 | 100 | 0 |
| 23 | 1000 | 100 | 0 |
| 24 | 1000 | 100 | 0 |
| 25 | 1000 | 100 | 0 |
| 26 | 1000 | 100 | 0 |
| 27 | 1000 | 100 | 0 |
| 28 | 1000 | 100 | 0 |
| 29 | 1000 | 100 | 0 |
| 30 | 1000 | 100 | 0 |
| 31 | 1000 | 100 | 0 |
| 35 | 1000 | 98 | 0 |
| 37 | 1000 | 99 | 0 |
| Comparative tests | | | |
| Comparative compound No. 2 | 1000 | 0 | 0 |

TABLE 8-continued

| Test compound No. | Concentration of active ingredient in the test solution (ppm) | Percentage of the disinfected seeds | Degree of phytotoxicity |
|---|---|---|---|
| Comparative compound No. 3 | 1000 | 53 | 0 |
| Comparative compound No. 5 (Iprodione) | 1000 | 95 | 0 |
| Untreated | — | 0 (45) | — |

Note 1: The Comparative compound No. 5 (Iprodione) is the same compound as that in the Test Example 2.
Note 2: The figure given in the parenthesis shows the percentage of the disease-incidennce seedlings in the untreated plots.

TEST EXAMPLE 9

Tests For Controlling Damping Off Disease Of Beet

A soil containing a predetermined concentration of the active ingredient was prepared by mixing thoroughly a soil (100 g) infested with the beet damping off disease (*Rhizoctonia solani*), with a dust formulation as prepared according to the Example 4. The soil thus prepared was charged into pots made of a plastic material. Seeds of beet (Variety; Sorolave) were sowed at a rate of 10 grains of the seeds per pot. The pots containing the seeds in the soil were kept at 24° C. 10 Days after the sowing of the seeds, the number of the damping-off killed seedlings of beet was counted. Rate (%) of the controlling effects of the test compound was evaluated according to the following equation:

$$\text{Rate (\%) of the controlling effects} = \left(1 - \frac{\text{percentage of the damping-off-killed seedlings in the treated plot}}{\text{percentage of the damping-off-killed seedlings in the untreated plot}}\right) \times 100$$

The tests were made in three replicates for each test plot. From the averaged value of the percentages of the damping-off-killed seedlings in the three pots was calculated the rate of the controlling effects of the test compound. Degree of the phototoxicity to beet was estimated according to the same standards as in the Test Example 1. The test results are shown in Table 9.

TABLE 9

| Test compound No. | Concentration of active ingredient in the soil (ppm) | Rate of the controlling effects (%) | Degree of phytotoxicity |
|---|---|---|---|
| 1 | 50 | 95 | 0 |
| 2 | 50 | 100 | 0 |
| 3 | 50 | 100 | 0 |
| 4 | 50 | 100 | 0 |
| 5 | 50 | 100 | 0 |
| 6 | 50 | 100 | 0 |
| 7 | 50 | 100 | 0 |
| 8 | 50 | 100 | 0 |
| 9 | 50 | 100 | 0 |
| 10 | 50 | 100 | 0 |
| 11 | 50 | 100 | 0 |
| 12 | 50 | 100 | 0 |
| 13 | 50 | 100 | 0 |
| 14 | 50 | 100 | 0 |
| 15 | 50 | 100 | 1 |
| 17 | 50 | 100 | 0 |
| 18 | 50 | 100 | 1 |
| 19 | 50 | 100 | 0 |
| 20 | 50 | 100 | 0 |
| 21 | 50 | 100 | 0 |
| 22 | 50 | 100 | 0 |
| 23 | 50 | 100 | 0 |
| 24 | 50 | 100 | 0 |
| 25 | 50 | 100 | 0 |
| 26 | 50 | 100 | 0 |
| 27 | 50 | 100 | 0 |
| 28 | 50 | 100 | 0 |
| 29 | 50 | 100 | 0 |
| 30 | 50 | 100 | 0 |
| 31 | 50 | 100 | 0 |
| 32 | 50 | 100 | 0 |
| 33 | 50 | 100 | 0 |
| 36 | 50 | 95 | 0 |
| 37 | 50 | 100 | 0 |
| Comparative tests | | | |
| Comparative compound No. 1 | 50 | 75 | 1 |
| Comparative compound No. 2 | 50 | 50 | 1 |
| Comparative compound No. 10 (PCNB) | 50 | 85 | 0 |
| Untreated | — | 0 (70) | — |

Note 1: The Comparative compound No. 10 (PCNB) is a commercially available fungicidal agent containing pentachloronitrobenzene.
Note 2: The figure given in the parenthesis shows the percentage of the damping-off-killed seedlings in the untreated plots.

INDUSTRIAL UTILITY OF THE INVENTION

As described hereinbefore, the new imidazole derivatives according to this invention are useful as the antibacterial and antifungal agent for use in the agriculture and horticulture, and they are suitable for control of the plant diseases.

We claim:

1. An imidazole derivative represented by the formula (I):

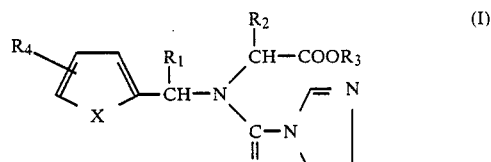

(I)

wherein $R_1$ denotes a hydrogen atom or a lower alkyl group of 1 to 6 carbon atoms, $R_2$ denotes a lower alkyl group of 1 to 6 carbon atoms, $R_3$ denotes an alkenyl group of 2 to 10 carbon atoms, a cycloalkyl group of 3 to 6 carbon atoms, and an alkoxyalkyl group of 3 to 6 carbon atoms, $R_4$ denotes a hydrogen atom or a lower alkyl group of 1 to 6 carbon atoms, and X denotes an oxygen atom or a sulfur atom.

2. An antibacterial and antifungal composition, which comprises as the active ingredient an imidazole derivative represented by the formula (I):

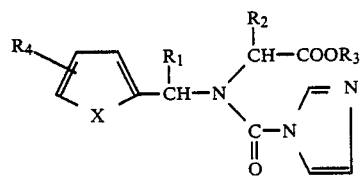

(I)

wherein $R_1$ denotes a hydrogen atom or a lower alkyl group of b 1 to 6 carbon atoms, $R_2$ denotes a lower alkyl group of 1 to 6 carbon atoms, $R_3$ denotes an alkenyl group of 2 to 10 carbon atoms, a cycloalkyl group of 3 to 6 carbon atoms, and an alkoxyalkyl group of 2 to 6 carbon atoms, $R_4$ denotes a hydrogen atom or a lower alkyl group of 1 to 6 carbon atoms, and X denotes an oxygen atom or a sulfur atom and an inert carrier.

3. An imidazole derivative of claim 1 where $R_1$ denotes a hydrogen atom, $R_2$ denotes methyl group, ethyl group or propyl group, $R_3$ denotes allyl group, 1-methyl-2-propenyl group, 2-butenyl group, 3-butenyl group, 4-pentenyl group or cyclopentyl group, $R_4$ denotes a hydrogen atom or methyl group, and X denotes an oxygen atom or a sulfur atom.

4. N-1-[1-(3-Butenylocoxycarbonyl) propyl]-N-(1-imidazolyl-carbonyl)-furfurylamine of the formula:

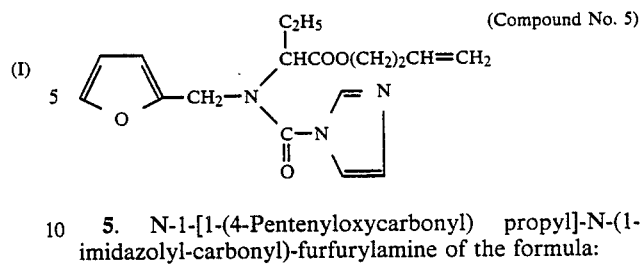

5. N-1-[1-(4-Pentenyloxycarbonyl) propyl]-N-(1-imidazolyl-carbonyl)-furfurylamine of the formula:

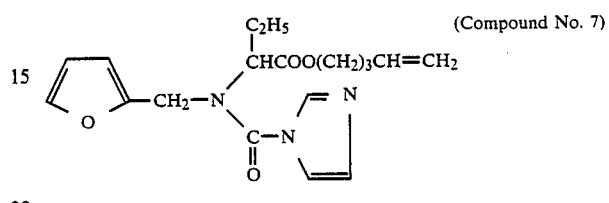

6. N-1-[1-(2-Butenyloxycarbonyl-butyl]-N-(1-imidazolyl-carbonyl) -furfurylamine of the formula:

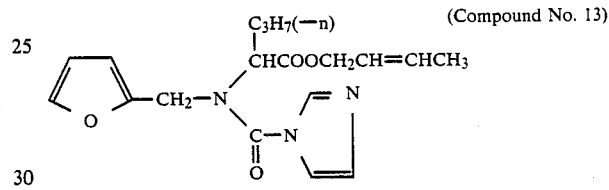

7. An imidazole derivative of claim 1 where $R_1$ denotes a hydrogen atom, $R_2$ denotes methyl group, ethyl group or a propyl group, $R_3$ denotes allyl group, 1-methyl-2-propenyl group, 2-butenyl group, 3-butenyl group or 4-pentenyl group, $R_4$ denotes a hydrogen atom, and X denotes an oxygen atom.

8. A method of disinfecting seeds of crop plants for prevention of fungal plant diseases, which comprises treating the seeds with an antifungally effective amount of an imidazole derivative of claim 7.

* * * * *